US005658855A

United States Patent [19]

Nalewaja et al.

[11] Patent Number: 5,658,855
[45] Date of Patent: Aug. 19, 1997

[54] ADJUVANTS FOR HERBICIDAL COMPOSITIONS

[75] Inventors: John D. Nalewaja, Fargo, N. Dak.; Robert Matysiak; Zenon Woznica, both of Poznan, Poland

[73] Assignee: North Dakota State University, Fargo, N. Dak.

[21] Appl. No.: 721,136

[22] Filed: Sep. 26, 1996

[51] Int. Cl.$^6$ .................................................. A01N 25/24
[52] U.S. Cl. .......................... 504/214; 504/215; 504/253; 504/116; 71/DIG. 1
[58] Field of Search ..................... 504/116, 214, 504/215, 253; 71/DIG. 1

[56] References Cited

U.S. PATENT DOCUMENTS

| | | | |
|---|---|---|---|
| 4,125,398 | 11/1978 | Roth | 71/115 |
| 4,227,911 | 10/1980 | Leonard et al. | 71/77 |
| 5,118,338 | 6/1992 | Moller | 71/86 |
| 5,266,553 | 11/1993 | Champion et al. | 504/206 |
| 5,341,932 | 8/1994 | Chen et al. | 206/254 |
| 5,346,704 | 9/1994 | Lajoie | 424/717 |
| 5,356,861 | 10/1994 | Gednalski et al. | 504/206 |
| 5,407,899 | 4/1995 | Howell | 504/152 |
| 5,409,885 | 4/1995 | Derian et al. | 504/116 |
| 5,411,932 | 5/1995 | Yoshida et al. | 504/132 |
| 5,430,005 | 7/1995 | Kassebaum et al. | 504/206 |
| 5,468,715 | 11/1995 | Joseph et al. | 504/101 |

OTHER PUBLICATIONS

S. D. Miller et al., "Barbarn–Aqueous Nitrogen Combinations for Wild Oat (*Avena fatua*) Control", *Weed Science*, vol. 26, Issue 4, (Jul.), 1978, pp. 344–348.

"Primisulfuron", *WSSA Herbicide Handbook—7th Edition*, 1994.
"Imazethapry", *WSSA Herbicide Handbook—7th Edition*, 1994, p. 166.
"Nicosulfuron", *WSSA Herbicide Handbook—7th Edition*, 1994, pp. 216–217.
J. D. Nalewaja et al., "Salts and Surfactants Influence Nicosulfuron Activity", *Weed Technology*, 1995, vol. 9:587–593.
G. Wanamarta et al., "Overcoming Antagonistic Effects of Na–Bentazon on Sethoxydim Absorption", *Weed Technology*, 1993, vol. 37:322–325.
P. J. Holloway, "Adjuvants For Foliage–Applied Agrochemicals: The Need For More More Science Not Serendipity", Fourth International Symposium on Adjuvants for Agrochemicals, Melbourne, Australia, 3–6 Oct. 1995 (FRI Bulletin No. 193), pp. 167–175.
J. D. Nalewaja et al., "Spray Carrier Salts Affect Heribicide Toxicity to Kochia (*Kochia scoparia*)", *Weed Technology*, 1993, vol. 7:154–158.
J. M. Green et al., "Surfactant Structure and Concentration Strongly Affect Rimsulfuron Activity", *Weed Technology*, 1993, vol. 7:633–640.

*Primary Examiner*—S. Mark Clardy
*Assistant Examiner*—Brian G. Bembenick
*Attorney, Agent, or Firm*—Fitch, Even, Tabin & Flannery

[57] ABSTRACT

Adjuvant compositions for herbicides comprising amine or ammonia compounds for adjusting the pH to the alkaline range, a neutral water soluble compound to provide a fertilizer action and a non-ionic surfactant and water. Herbicidal compositions using the adjuvant in combination with the herbicide are also included as well as methods for controlling weeds or undesirable vegetation by application of those compositions thereto.

18 Claims, No Drawings

ADJUVANTS FOR HERBICIDAL COMPOSITIONS

BACKGROUND OF THE INVENTION

1. Field of the Invention

This invention relates to new, water soluble adjuvant compositions for use in spray carriers containing postemergence herbicides, which are used to control weeds or other undesired vegetation in crops.

2. Description of the Prior Art

Herbicides used in controlling weeds or undesired vegetation in agriculture are customarily applied by postemergence spraying of a herbicide on the crop. The spray carrier for the herbicide is usually a water based solution containing an effective amount of known herbicide.

Adjuvants are commonly added to herbicidal spray solutions to enhance postemergence weed control and/or to reduce spray drift during herbicide applications.

Postemergence weed control requires that the spray containing the herbicide be retained on the weed surface for that purpose. To obtain that result, many "sticker" compositions or agents, including methylated vegetable oils or mineral based oils and wetting (surface/active) agents are marketed for spray solution adherence of the herbicide by the weeds and in addition help retain droplets of the spray solution on the plant and to penetrate into the plant.

In addition to spray retention by the weed, other additives in the form of liquid nitrogen based fertilizer solution have been found, for example, to enhance the control of wild oats by herbicides such as Barban. Miller et al., *Weed Science*, 1978, Vol. 4, pp. 344–348. Recently surfactants have been combined with liquid fertilizers (usually 28% nitrogen and comprising a mixture of 50% ammonium nitrate and 50% urea). The results however are variable depending on surfactants used and nitrogen fertilizer employed. It was found that certain salts and surfactants influence nicosulfuron, for example, and its herbicide activity. Nalewaja et al., *Weed Technology*, 1995, Vol. 9, pp. 587–593.

Some acidic additives have previously been used which are designed to lower pH and enhance the acidity of the spray carrier water formulation which was believed to both benefit herbicide adsorption and also to prevent alkaline hydrolysis of certain insecticides. Acids and buffering agents are sometimes also used to reduce antagonism from alkaline salts found in the spray carrier water.

It has been noted that adjuvants differ greatly in herbicide enhancement depending on the specific surfactant and the herbicide used in some cases resulting in decreased performance. Halloway, *4th International Symposium on Adjuvants for Agrochemicals*, 1995, FR. & Bulletin, No. 193).

SUMMARY OF THE INVENTION

The present invention relates to adjuvant compositions for use in the spray carrier of postemergence herbicides applied as an aqueous spray solution to crops infested with undesired weeds or plants to control the same.

Broadly, the adjuvant compositions of the invention comprise (A) an amine or ammonia compound for adjusting the pH to the alkaline range, (B) a neutral water soluble nitrogen compound to provide a fertilizer action and (C) a non-ionic surface active agent with a high Hydrophilic-Lipophilic Balance (HLB), which functions as a spreader or sticker and penetrant for use with postemergence herbicides and (D) water.

Broadly, about 1% of the adjuvant compositions of the present invention are diluted with water (99%) to which is added the desired herbicide in herbicidally effective amounts on an area of application basis, customarily less than about 2% or less by weight of the aqueous spray solution and applied to the crop for weed control purposes. A preferred amount of herbicide ranges for the tables herein follow that procedure. As discussed above, the herbicide of choice is customarily added to the final aqueous spray solutions at the label recommended amount, for example, diluted to provide application rates of broadly from 0.12 to 2 ounces and preferably 0.25 to 2 ounces per acre of the active herbicide ingredient.

More particularly, the adjuvant of the present invention is a three component mixture comprising:

A) an alkaline amine pH regulator to provide an alkaline pH of the final spray solution of above about 7 up to about 9. The upper limit of pH chosen should not be so high as to result in hydrolysis of the herbicidal use. The lower pH limit should be slightly above 7 in the alkaline range, for example, 7.25. Alkaline components which contain calcium or sodium cations should be avoided since these are considered antagonistic to many herbicides. Preferred alkaline compounds used to provide an alkaline spray solution are various amine or ammonium compounds which are employed in amounts of up to about 16% by weight of the adjuvant composition. Useful amine type compounds are ammonium hydroxide, and water soluble amines. Amines such as monoethanolamine, diethanolamine, triethanolamine and 2-amino-2-ethyl-1,3-propanediol are examples of preferred pH regulators.

B) The second component (B) of the adjuvant composition is a neutral ammonium salt composition including preferably ammonium nitrate, ammonium chloride, and ammonium sulfate. The neutral ammonium salt compound can vary between 5 to 30% by weight of the adjuvant composition up to as high as about 50% by weight. The neutral ammonium salt provides a readily available nitrogen fertilizer component and enhances the effect of certain herbicides in weed control.

C) The third component (C) of the adjuvant composition is a non-ionic surfactant preferably secondary or linear (primary) alcohols or other non-ionic surfactants having a high HLB (Hydrophilic-Lipophilic Balance) broadly above about 10 to about 16; preferably between 12 and 16. They may also be block copolymers of various HLB's. Examples of suitable non-ionic surfactants having a high HLB are GENAPOL 24-L-75, an ethoxylated alcohol, product of Hoechst Celanese Corp., (HLB 10.9); Pluronics, block copolymers of propylene oxide and ethylene oxide, products of BASF Corp., (P103, HLB up to 12; P104, HLB 12–18); Tween 20, polyoxethylene (20) sorbitan monolaurate, product of ICI Surfactants, (HLB 16.7); and Tergitol 15-S-9, a secondary alcohol ethoxolate, a product of Union Carbide Corp., (HLB 13.3). The non-ionic surfactant component ranges between 15 to 80% by weight of the adjuvant, with a preferred range of 20 to 50% by weight of the adjuvant mixture.

D) The balance to make 100% of the adjuvant mixture is water.

The adjuvant is customarily formulated and sold in two and one half (2½) gallon or larger batches which are used to make up the spray mixture which includes spray water (about 99%) and a herbicidally effective amount of a postemergence herbicide. Preferably, the herbicides employed in this invention are selected from the group consisting of:

Dicamaba (sold under the tradename Banvel D) which is the compound.

3,6-dichloro-2-methoxy benzoic acid

Nicosulfuron (sold under the tradename Accent) which is the compound

[[[[(4,6-demethoxy-2-pyrimidinyl)amino]carbonyl]amino]sulfonyl-N,N-dimethyl-3-pyridine carboxy amide;

Imazethapyr (sold under the tradename Pursuit) which is the compound

2-[4,5-dihydro-4-methyl-4-(1-methylethyl)-5-oxo-1H-imidazol-2-yl]-5-ethyl-3-pyridinecarboxylic acid;

Rimsulfuron (sold under the tradename Matrix), which is the compound

N-[[(4,6-dimethoxy-2-[pyrimidinyl)-2-amino) carbonyl]-3-(ethyl sulfonyl)-2-pyridine sulfonamide);

Primisulfuron—(also sold under the tradename Beacon) which is the compound methyl-2-[[[[[4,6-bis(difluoromethoxy)-2-pyrimidinyl]amino]carbonyl]amino]sulfonyl]benzoate.

This invention includes aqueous herbicidal spray compositions containing adjuvant composition of this invention comprising.

(A) an amino alkaline pH regulator compound selected from the group consisting of ammonium hydroxide; monoethanolamine, diethanolamine, triethanolamine, and 2-amino-2-ethyl-1,3-propanediol and mixtures thereof in sufficient amount to provide a pH of from about 7.25 to about 9 in the final diluted aqueous composition;

(B) a neutral ammonium salt selected from the group consisting of ammonium nitrate, ammonium chloride and ammonium sulfate, in an amount of from about 5 to 50% by weight of said adjuvant composition;

(C) a non-ionic surface active agent having an HLB of from about 10 to about 16 in an amount of from about 15 to 80% by weight of said adjuvant composition;

(D) water to make 100%;

(E) an effective amount of a postemergence herbicide; and (F) additional water to make up the final spray solution.

The post emergence herbicidal aqueous spray composition utilizing the adjuvant compositions of this invention comprise from about 0.15 to 0.8 and preferably 0.2 to 0.5 of a non-ionic surfactant having a high Hydrophylic-Lipophylic Balance (HLB); an alkaline amine type pH regulator selected from the group consisting of ammonium hydroxide, monoethyanol amine, diethanolamine, triethanolamine and 2-amino-2-ethyl-1,3-propanediol in an amount to provide a pH of from about 7.25 to about 9 in the final aqueous solution; from about 0.05 to 0.5% of a neutral ammonium salt selected from the group consisting of ammonium nitrate, ammonium chloride and ammonium sulfate; and from about 0.005 to 2% of a herbicide selected from the group consisting of 2[[[[(4,6-dimethoxy-2-pyrimidinyl)amino]carbonyl]amino]sulfonyl-N,N-dimethyl-3-pyridine dicarboxyamide; 2-[4,5-dihydro-4-methyl-4-(1-methyl(ethyl)-5-oxo-1H-imidazol-2-yl]-5-ethyl-3-pyridine carboxylic acid; N-[[(4,6-dimethoxy-2-[pyrimidinyl)-2-amino) carbonyl]-3-(ethyl sulfonyl)-2-pyridine sulfonamide; and methyl-2-[[[[[4,6-bis(difluoromethoxy)-2-pyrimidinyl]amino]carbonyl]amino]sulfonyl]benzoate and water to make 100% of said aqueous spray solution.

The following tables illustrate various examples of the adjuvant compositions of the present invention and their use in weed control. The compositions illustrating the adjuvant compositions of this invention used in postemergence herbicidal applications are identified in the tables with the letters "ND". The application rate of the herbicide used is expressed in oz./acre which is ounces per acre of active (herbicide) ingredient. In the context of this invention, the terms "weed" or "weeds" is intended to include common or naturally occurring weeds or in some cases undesired adventitious crop species.

TABLE 1

Grass species control with nicosulfuron at 0.12 and 0.25 oz/A as influenced by adjuvants, North Dakota field experiments 1994 and 1995.

| | | 1994[b] | | | | 1995[b] | | | Fargo | Cass | |
| | | Fargo | Will | Minot | G.F. | Fargo 1 | | Will | 2 | Gr- | |
| Adjuvant[a] | Nico[c] | Yeft | Grft | Primi | Primi | Primi | Yeft | Grft | Yeft | Yeft | Avg. |
| | | | | | | % control | | | | | |
| Scoil ® 1% | 0.12 | 75 | 85 | 83 | 82 | 77 | 76 | 74 | 86 | 71 | 79 |
| Scoil ® 1% | 0.25 | 92 | 91 | 94 | 90 | 91 | 93 | 71 | 94 | 84 | 89 |
| ND-94-4 1% | 0.12 | 85 | 93 | 87 | 88 | 82 | 82 | 65 | 82 | 56 | 80 |
| ND-94-4 1% | 0.25 | 89 | 93 | 93 | 90 | 91 | 89 | 81 | 90 | 88 | 89 |
| LSD 5%[(d)] | | 8 | 11 | 7 | 5 | 10 | 9 | 18 | 6 | 13 | |

[a]Scoil ® (AGSCO) is a methylated vegetable oil adjuvant, ND-94-4 is a high pH (type) formulation of the invention adjuvant with Tergitol 15-S-9 surfactant and ammonium nitrate. Percentages are amount of adjuvant in the spray solution. ND-94-4 contained Tergitol 15-S-9 (25%), ammonium nitrate (25%), triethanolamine (8%) and water (42%) and provided a pH of about 8 when formulated in spray solution at a ratio of 1 part adjuvant and 99 parts water.
[b]Will, Williston; Cass, Casselton; G. F., Grand Forks; Avg., Average; yeft = yellow foxtail, Primi = proso millet a grft = green foxtail.
[c]"Nico" - nicosulfuron applied at indicated rate per acre.
[d]LSD is Least Significant Difference.

TABLE 2

Rox orange sorghum control with nicosulfuron at 0.17 oz/A
and primisulfuron at 0.19 oz/A as influenced by adjuvants,
Manhattan, KS 1994.

| Adjuvant[a] | Nicosulfuron | Primisulfuron |
|---|---|---|
| | % Rox sorghum control | |
| Activator 90 ® 0.25% | 69 | 71 |
| Methoil ® 1% | 75 | 79 |
| Prime Oil ® 1% | 74 | 92 |
| ND-94-1 0.5% | 89 | 88 |
| ND-94-1 1% | 91 | 93 |
| LSD 5% | 13 | |

[a]Activator 90 ® is a non-ionic surfactant of alkylpoloxyethylene ethers and free fatty acids from Loveland Industries. Methoil ® is a methylated vegetable oil and Prime Oil ® is a petroleum oil both from Terra International, and ND-94-1 is a three-component high pH adjuvant which contains Genapol ® 24-L-75 (25%) (HLB 10.9), ammonium nitrate (25%), 2-amino-2-ethyl-1, 3-propanediol (4%), and water (46%) which produces a pH of 8 in the final aqueous spray solution of the adjuvant when mixed with water to make the final spray solution. Nicosulfuron and Primsulfuron are applied at indicated rate in ounce per acre.

The uniqueness and importance of the high pH three component adjuvant for consistent nicosulfuron activity under various application conditions are indicated from several experiments. Herbicide effectiveness often varies for unknown reasons as indicated by the almost equal effectiveness of the high pH three-component ND-94-4 and Scoil® in Table 1, but greater effectiveness of ND-94-4 in Table 3.

TABLE 3

Nicosulfuron (0.25 oz. active ingredient per acre) control of weeds in corn, Casselton, North Dakota 1994.

| | | | 6/30 | | | 8/5 | | |
|---|---|---|---|---|---|---|---|---|
| Adjuvant[a] | Rate % | Corn | Grft/ Yeft | Coco | Colq % | Yeft | Cocb | Colq |
| Scoil ® | 1 | 0 | 60 | 26 | 35 | 62 | 26 | 23 |
| ND-94-4 | 1 | 0 | 85 | 53 | 60 | 80 | 80 | 66 |
| ND-94-4 (-pH) | 1 | 0 | 48 | 14 | 14 | 51 | 55 | 35 |
| LSD 5% | | NS | 13 | 21 | 19 | 12 | 37 | 30 |

[a]Adjuvant rate expressed as percent of total spray solution. The adjuvant ND-94-4 is Tergitol 15-S-9 (25%), ammonium nitrate (25%), and pH regulator triethanolamine (8%) and water (42%) and gave a final spray solution pH of about 8 and ND-94-4 (-pH) does not contain triethanolamine and had a spray solution pH below 7, in the acidic range. The adjuvant ND-94-4 and Scoil ® (methylated vegetable oil adjuvant) are added to the carrier with the herbicide and nicosulfuron at 0.25 oz./acre to prepare the final aqueous spray solution spplied at the "Rate" shown in the table.

Yeft, yellow foxtail, Grft, green foxtail; Cocb, common cocklebur, Colq. common lambsquarters.

The importance of high pH to nicosulfuron activity also is shown in Table 4 where ND-94-4 (–pH) without the pH component was less effective than the comparable ND-94-4 containing the high pH component.

The high pH component is especially important to efficacy when low spray volumes are used and, thus, would help provide consistent herbicide performance with the various spray volumes used commercially (Table 4).

TABLE 4

Large crabgrass percentage fresh weight reduction (% FWR)
using nicosulfuron at 0.25 oz/A as influenced by spray carrier
pH and spray volume expressed as gallons of spray per acre
(gpa), greenhouse tests.

| Surfactant | pH | Spray Volume gpa | Large Crabgrass % FWR |
|---|---|---|---|
| Tergitol 15-S-9 | 4 | 8.5 | 36 |
| Tergitol 15-S-9 | 9 | 8.5 | 73 |
| Tergitol 15-S-9 | 4 | 26 | 83 |
| Tergitol 15-S-9 | 9 | 26 | 83 |
| LSD 5% | | | 4 |

The Tergitol 15-S-9 (Union Carbide) final spray solutions present in an amount of 0.25% (v/v). The test at pH 4 was the herbicide, surfactant and distilled water alone and the test at pH 9 was obtained using ammonium hydroxide titrated with the spray solution. "FWR" is Fresh Weight Reduction of the crabgrass.

The importance of high pH to efficacy of nicosulfuron at low spray volume is shown in Table 5 where Tergitol 15-S-9 was as effective at 8.5 gallons per acre spray volume as Scoil® at 17 gallon per acre. Further, the data in Table 5 indicate that the loss in nicosulfuron effectiveness from a reduction in percentage adjuvant in the spray was greater for Scoil® than ND-94-4. Thus, the high pH adjuvant would provide more effective weed control over various spray conditions and could allow for use of lower amounts of adjuvant. The greater effectiveness of ND-94-4 at low percentage of the spray was confirmed under field conditions (Table 6). The use of less adjuvant would provide economic benefits and natural resource conservation.

Influence of adjuvant concentration and spray volume on nicosulfuron (0.25 oz/A) toxicity to large crabgrass in the greenhouse.

TABLE 5

| | Spray Volume, gallons per acre | | | |
|---|---|---|---|---|
| | 8.5 gpa | | 17 gpa | |
| Adjuvant | Scoil ®[a] | ND-94-4[a] | Scoil ® | ND-94-4 |
| | % fresh weight reduction | | | |
| 0.25% | 56 | 84 | 82 | 90 |
| 0.5% | 71 | 86 | 89 | 93 |
| 1.0% | 80 | 91 | 92 | 93 |
| LSD 5% | | 5 | | |

[a]Scoil ® is a methylated vegetable oil; ND-94-4 a high pH (8) three-component adjuvant comprising 8% triethanolamine pH regulator to provide a final spray solution of pH 8, 25% neutral ammonium nitrate salt, 25 weight % Tergitol 15-S-9 non-ionic surfactant, and 42% water. The adjuvant and herbicide are diluted with water to make up the final spray solution, at percentages and application rates in oz/acre, respectively. "Nico" = Nicosulfuron.

TABLE 6

Proso millet control with nicosulfuron at 0.25 oz/A as influenced by adjuvant concentration as shown by tests seen at Torrington, Wyoming, 1995.

| Adjuvant* | | 2 WAT | 5 WAT |
|---|---|---|---|
| Type | Final Spray Concentration | % | |
| Scoil® | 1.25% | 96 | 92 |
| ND-94-4 | 0.625% | 100 | 93 |
| ND-94-4 | 1.25% | 100 | 97 |

ND-94-4 is a high pH type formulation of the adjuvant of the invention containing Tergitol 15-S-9 surfactant (Union Carbide) (25%), ammonium nitrate (25%), water 42% and triethanolamine (8%), which when diluted with water provided a final spray solution with a pH of about 8. Nicosulfuron applied at rate of 0.25 oz/acre when mixed with water using Scoil® at 1.25% solution and ND-94-4 at final spray concentrations of 0.625% and 1.25%.

The adjuvant compositions disclosed herein are useful as relatively low cost compositions for preparing herbicidal compositions used for aqueous spray application to control weeds or undesired vegetation with known herbicides. The materials used in the adjuvants generally enhance herbicidal effectiveness when applied under a broad range of conditions, including for example when formulated with local water containing sodium bicarbonate which frequently displays antagonism to the effectiveness of many herbicides. The compositions of the invention are also especially valuable since they have minimal effect on the environment and are of low toxicity to animal life.

What is claimed is:

1. An adjuvant composition for use in aqueous herbicidal spray compositions comprising:
   (A) an amine alkaline compound in an amount to provide an alkaline pH of above about 7 to about 9 when formulated in a final spray composition;
   (B) a neutral ammonium salt compound in an amount of from 5 to 30% by weight of the adjuvant;
   (C) a non-ionic surfactant having a high Hydrophilic-Lipophilic Balance (HLB), in an amount of from about 15 to 80% by weight of the adjuvant; and
   (D) sufficient water to make 100 percent of the adjuvant composition.

2. An adjuvant composition according to claim 1 wherein the amine alkaline compound of component (A) comprises up to about 16% by weight of the composition.

3. An adjuvant composition according to claim 1 wherein the amine alkaline compound (A) is selected from the group consisting of ammonium hydroxide, and organic water soluble amines.

4. An adjuvant composition according to claim 1 wherein the amine alkaline compound (A) is selected from the group consisting of ammonium hydroxide, monoethanolamine, diethanolamine, triethanolamine and 2-amino-2-ethyl-1,3-propanediol and mixtures thereof.

5. An adjuvant composition according to claim 1 wherein the neutral ammonium salt compound (B) is selected from the group of ammonium nitrite, ammonium chloride, ammonium sulfate and mixtures thereof.

6. An adjuvant composition according to claim 1 wherein the non-ionic surfactant has an HLB of from about 10 to about 16.

7. An adjuvant composition according to claim 1 wherein the non-ionic surfactant (C) is a primary or secondary alcohol.

8. An adjuvant composition according to claim 1 wherein the non-ionic surfactant is a block copolymer.

9. An adjuvant composition according to claim 7 wherein the non-ionic surfactant (C) is present in an amount of from about 20 to 50% by weight of the adjuvant composition.

10. An adjuvant composition according to claim 1 wherein the alkaline compound (B) is present in an amount sufficient to provide a pH of at least about 7.25 when formulated in a final aqueous spray solution.

11. A composition according to claim 1 further characterized by the absence of significant herbicidally antagonistic amounts of calcium or sodium cations.

12. An aqueous postemergence herbicidal spray composition which comprises an adjuvant composition comprising:
    (A) an amine alkaline pH regulator compound selected from the group consisting of ammonium hydroxide, monoethanolamine, diethanolamine, triethanolamine, and 2-amino-2-ethyl-1,3-propanediol and mixtures thereof in sufficient amount to provide a pH of from about 7.25 to about 9 in the final diluted aqueous composition;
    (B) a neutral ammonium salt selected from the group consisting of ammonium nitrate, ammonium chloride and ammonium sulfate, in an amount of from about 5 to 50% by weight of said adjuvant composition;
    (C) a non-ionic surface active agent having an HLB of from about 10 to about 16 in an amount of from about 15 to 80% by weight of said adjuvant composition;
    (D) water to make 100%;
    (E) an effective amount of a postemergence herbicide; and
    (F) additional water to make up the final spray solution.

13. An herbicidal composition according to claim 11 wherein the herbicide (E) is selected from the group consisting of 2[[[[(4,6-dimethoxy-2-pyrimidinyl)amino]carbonyl]amino]sulfonyl-N,N-dimethyl-3-pyridine dicarboxyamide; 2-[4,5-dihydro-4-methyl-4-(1-methyl(ethyl)-5-oxo-1H-imidazol-2-yl]-5-ethyl-3-pyridine carboxylic acid; N-[[(4,6-dimethoxy-2-[pyrimidinyl)-2-amino) carbonyl]-3-(ethyl sulfonyl)-2-pyridine sulfonamide; and methyl-2-[[[[4,6-bis(difluoromethoxy)-2-pyrimidinyl]amino]carbonyl]amino]sulfonyl]benzoate.

14. A composition according to claim 12 wherein the herbicide (E) ranges from about 0.005 to about 2% of the final diluted aqueous spray composition.

15. A method of controlling weeds which comprises applying an herbicidal composition of claim 13 postemergence to a weeds and/or other undesired vegetation.

16. A post emergence herbicidal aqueous spray composition comprising from about 0.2 to 0.5% of a non-ionic surfactant having a high Hydrophylic-Lipophylic Balance (HLB); an alkaline amine type pH regulator selected from the group consisting of ammonium hydroxide, monoethanol amine, diethanolamine, triethanolamine and 2-amino- 2-ethyl-1,3-propanediol in an amount to provide a pH of from about 7.25 to about 9 in the final aqueous solution; from about 0.05 to 0.5% of a neutral ammonium salt selected from the group consisting of ammonium nitrate, ammonium chloride and ammonium sulfate; and from about 0.005 to 2% of a herbicide selected from the group consisting of 2[[[[(4,6-dimethoxy-2-pyrimidinyl)amino]carbonyl]amino]sulfonyl-N,N-dimethyl-3-pyridine dicarboxyamide; 2-[4,5-dihydro-4-methyl-4-(1-methyl(ethyl)-5-oxo-1H-imidazol-2-yl]-5-ethyl-3-pyridine carboxylic acid; N-[[(4,6-dimethoxy-2-[pyrimidinyl)-2-amino)carbonyl]-3-(ethyl sulfonyl)-2-pyridine sulfonamide; and methyl-2-[[[[[4,6-bis (difluoromethoxy)-2-pyrimidinyl]amino]carbonyl]amino]sulfonyl]benzoate and water to make 100% of said aqueous spray solution.

17. A method of controlling weeds or other undesired vegetation which comprise applying to said weeds or undesired vegetation an aqueous herbicidal composition according to claim 16.

18. An herbicidal spray solution comprising about 1% of an aqueous adjuvant composition according to claim 1, an effective amount of an herbicide and water to make 100% of said composition.

* * * * *

UNITED STATES PATENT AND TRADEMARK OFFICE
CERTIFICATE OF CORRECTION

PATENT NO. : 5,658,855
DATED : August 19, 19976
INVENTOR(S) : John D. Nalewaja et al.

It is certified that error appears in the above-indentified patent and that said Letters Patent is hereby corrected as shown below:

ON THE TITLE PAGE:

Item:      [73], change the Assignee from "North Dakota State University" to --NDSU-Research Foundation--.

IN THE CLAIMS:

Column 8, line 60, delete "a" after "to"

Column 8, line 64, change "Hydrophylic-Lipophylic" to --Hydrophilic-Lipophilic--.

Signed and Sealed this

Sixth Day of January, 1998

Attest:

BRUCE LEHMAN

*Attesting Officer*         *Commissioner of Patents and Trademarks*

UNITED STATES PATENT AND TRADEMARK OFFICE
CERTIFICATE OF CORRECTION

PATENT NO. : 5,658,855
DATED : August 19, 1997
INVENTOR(S) : John D. Nalewaja et al.

It is certified that error appears in the above-indentified patent and that said Letters Patent is hereby corrected as shown below:

ON THE TITLE PAGE:

Item: [73], change the Assignee from "North Dakota State University" to --NDSU-Research Foundation--.

IN THE CLAIMS:

Column 8, line 60, delete "a" after "to"

Column 8, line 64, change "Hydrophylic-Lipophylic" to --Hydrophilic-Lipophilic--.

This certificate supersedes Certificate of Correction issued January 6, 1998.

Signed and Sealed this

Second Day of June, 1998

*Attest:*

BRUCE LEHMAN

*Attesting Officer*     Commissioner of Patents and Trademarks